United States Patent [19]
Uhlendorf et al.

[11] Patent Number: 5,410,516

[45] Date of Patent: Apr. 25, 1995

[54] ULTRASONIC PROCESSES AND CIRCUITS FOR PERFORMING THEM

[75] Inventors: Volkmar Uhlendorf; Thomas Fritzsch; Joachim Siegert, all of Berlin, Germany

[73] Assignee: Schering Aktiengesellschaft, Berlin and Bergkamen, Germany

[21] Appl. No.: 76,221

[22] Filed: Jun. 14, 1993

Related U.S. Application Data

[63] Continuation of Ser. No. 684,900, Mar. 9, 1992, abandoned.

[30] Foreign Application Priority Data

Sep. 1, 1988 [DE] Germany .................. 38 29 999.2

[51] Int. Cl.⁶ .............................................. G01S 7/52
[52] U.S. Cl. ......................................................... 367/7
[58] Field of Search ............................. 367/7, 11, 90; 73/861.04, 861.27, 155; 364/413.25; 358/112; 128/660.01, 660.07, 661.07, 662.02

[56] References Cited

U.S. PATENT DOCUMENTS

| | | |
|---|---|---|
| 3,640,271 | 2/1972 | Horton . |
| 4,452,082 | 6/1984 | Miwa . |
| 4,483,345 | 11/1984 | Miwa . |
| 4,532,812 | 8/1985 | Birchak ............... 73/861.04 |
| 4,610,255 | 9/1986 | Shimura et al. . |
| 5,255,683 | 10/1993 | Monaghan ........... 128/662.02 |

OTHER PUBLICATIONS

Germain et al., "Generation and detection of high--order harmonics...", J. Acoust. Soc. Am. 83 (3) Mar. 1988, pp. 942–949.

Law et al., "Ultrasonic determination of the nonlinearity parameter..." J. Acoust. Soc. Am. 69 (4), Apr. 1981, pp. 1210–1212.

*Primary Examiner*—Daniel T. Pihulic
*Attorney, Agent, or Firm*—Millen, White, Zelano & Branigan

[57] ABSTRACT

A process for selective graphic representation and/or evaluation of the Doppler spectrum of objects limitedly resistant to sonic intensity, for example biological organs and tissues, by an ultrasonic process wherein a material is introduced in the examination area to be acoustically irradiated, nonlinear oscillations are produced in the examination area by irradiated ultrasonic waves and the signal is evaluated by an ultrasonic converter. Also, a circuit for carrying out the above process is disclosed.

17 Claims, 9 Drawing Sheets

$f_0 = 4$ MHz, +15 dBm AT THE SOUND HEAD

→ TIME

FIG. 5

$f_0$ = 4.0 MHz, +15 dBm AT THE SOUND HEAD

TIME

FIG. 6

$f_0 = 3.0$ MHz, +15 dBm AT THE SOUND HEAD $2_0 \times f$ $3_0 \times f$

→ TIME

FIG. 7

$f_0 = 4.0$ MHz, +20 dBm AT THE SOUND HEAD $\frac{1}{2} \times f_0$  $\frac{3}{2} \times f_0$ $2 \times f_0$

FIG. 8 →TIME $f_0 = 4.0$ MHz, +15 dBm AT THE SOUND HEAD

FIG. 9 →TIME

FIG. 10

ULTRASONIC PROCESSES AND CIRCUITS FOR PERFORMING THEM

This application is a continuation of application Ser. No. 07/684,900, filed Mar. 9, 1992, now abandoned.

The invention relates to ultrasonic processes according to the introductory clause of claims 1 or 2 and circuits for performing them.

In ultrasonic technology, ultrasonic waves are irradiated in an examination area for selective graphic representation and/or evaluation of the Doppler spectrum. Combined transceiver sound heads are usually used in the processes and equipment for material testing and for examination of biological tissues. In this way, a sound frequency ($f_o$), which is the same for the sending and receiving, is determined by the crystals of the oscillator and the equipment electronics. A typical 5 MHz sound head has a frequency range of about 3–7 MHz with a maximum at $f_o=5$ MHz. In the same frequency range, the reflected and/or backscattered signal is received with the pulse-echo process. Such equipment and processes are also used in the examination of biological tissue with the use of ultrasonic contrast media. Signal portions lying outside the specified frequency range, such as, for example, oscillations being in a harmonic ratio to the sending frequency, are not used for the graphic representation of the examination object and other analyses, such as, e.g., Doppler measurements. In the previously known processes and equipment systems, several sound heads, which are changed during the examination, are further used to cover a sizable frequency range.

Improving the image quality by using harmonic multiples of the excitation frequency in ultrasonic microscopy is known from the bibliographical reference L. Germain, J. O. N. Cheeke, (J. Accoust. Soc. Am. E3 (1988) 942). For this purpose, however, ultrasonic waves with very high amplitude have to be irradiated to produce nonlinear oscillations in the path in the examination area, and by this nonlinearity, a transmission of energy from the oscillations with the basic frequency takes place in higher harmonic oscillations.

But such a process cannot be used in the ultrasonic examination with low frequencies, for example, in the range of 1–10 mHz of objects which are not resistant to high sound intensities, such as, especially, biological tissues.

The object of the invention is to broaden the range of use of ultrasonic processes for objects, limitedly resistant to sound intensity, especially biological tissues, for selective graphic representation and evaluation of the Doppler spectrum and to provide circuits for performing these processes.

According to the invention, this object is achieved in that a material is introduced in the examination area to be acoustically irradiated, with which nonlinear oscillations in this area are produced by irradiated ultrasonic waves, a broadband, acoustically highly damped, electrically matched ultrasonic converter with one or more controllable converter elements assembled individually or in groups, which corresponds to a frequency band which, in addition to the excitation frequency, comprises at least $\alpha/2$ and/or $\alpha/3$ and/or $\alpha/4$ times excitation frequency ($f_o$), with $\alpha$=whole number, is excited for acoustic irradiations of the examination area and the excitation frequency and/or at least one of $\alpha/2$, $\alpha/3$, $\alpha/4$ times it are evaluated from the ultrasonic signal received by the ultrasonic converter, reflected from the examination area or backscattered from the latter.

If $\alpha$ is an even-numbered multiple of the denominator, the corresponding oscillations are the harmonics. If $\alpha<$the denominator, these oscillations are called subharmonics in the literature. If $\alpha>$the denominator, ultraharmonic oscillations are involved.

By introducing materials or media in the examination area to be acoustically irradiated, which produce a nonlinearity, it is surprisingly possible, even in low sonic intensities, which are not harmful, to obtain intensive and strongly frequency-shifted stray and/or transmission signals in addition to excitation frequency, $f_o$. These stray and/or transmission signals are intensive particularly in harmonics (2 $f_o$, 3 $f_o$), subharmonics ($\frac{1}{2} f_o$, $\frac{1}{3} f_o$, $\frac{3}{4} f_o$) and ultraharmonics (3/2 $f_o$, 5/4 $f_o$ ... ) of the excitation frequency. With this process, irradiation can be performed with low frequencies, so that a greater penetration depth is obtained and receiving signals of higher frequencies can be evaluated.

In an advantageous way, a selective evaluation of the signal portions influenced by the fed materials or media as well as a selective display of the areas filled with these media is possible, without a previously necessary subtraction being made between two or more states recorded before and after the application of the materials or media. Especially, the Doppler effect caused can be evaluated independently of artifacts.

Nonlinear stray elements are advantageously introduced in the examination area. But in the examination area, a nonlinear ultrasonic contrast medium can also be introduced in the form of a solution or suspension and especially microbubbles or agents producing microbubbles.

The introduction of a microbubble suspension with a concentration of $10^{-3}\%$ by weight to 30% by weight of dry substance in a suspension medium leads to good results, and, surprisingly, the low lower limit of $10^{-3}\%$ by weight is attained with the process according to the invention and the circuit according to the invention.

In the process according to the invention, the sonic converter is advantageously excited by a function generator, with which HF bursts with adjustable amplitude and adjustable center frequency ($f_r$) are produced in the range of 0.3 MHz to 22 MHz, preferably 1 MHz to 11 MHz, and with 0.5 to 20, preferably 1–5, periods. In this case, it has been shown as especially advantageous to evaluate frequencies which are smaller than sonic converter (transmitter) center frequency $f_r$.

In the evaluation, it is advantageous, by a computer-controlled gate circuit, to select at least one period and to determine the related frequency spectrum in an analog or digital manner. In this case, the time window length and the number of periods per burst are adjusted between the optimum frequency resolution and optimum high-sensitivity resolution.

With the process according to the invention, Doppler effects can advantageously be evaluated in harmonics of the excitation frequency and in the mixed products, such as, the upper sideband in 2-frequency excitations. This permits the representation of slower flows without disturbances by movements of the vessel wall.

An improved penetration depth and/or space resolution, which is very advantageous in graphic representation and in Doppler measurements, further results in the evaluation of harmonic signal portions or signals in the upper sideband.

The circuit, according to the invention, for performing the process described above exhibits a function generator whose output is connected with the oscillator of an acoustically highly damped, electrically matched, broadband converter element by an T/R transceiver) circuit synchronized by the function generator, which is downstream from a signal processing system.

In another embodiment of the circuit, the function generator is connected to the input of a converter whose output is connected to a signal processing system.

In the first case mentioned, the burst produced by the function generator in the "sending" circuit of the T/R switch is transmitted to the oscillator of the converter and the signal received by the converter is transmitted in the switched-on "receiving" position of the T/R circuit to the evaluating system. In the second case, the input and output are separated in the converter so that a T/R switch is not necessary.

A converter element, whose center frequency $f_r$ is greater than the upper limit of the operating range, is used with special advantage. This converter element is designed so that, as a function of the frequency in the frequency range below excitation or center frequency $f_r$, the sonic intensity radiated by the converter element exhibits a positive first derivative with respect to the frequency, which is approximately constant especially in the operating range, or so that the sonic intensity which is in the operating range itself has a constant value. By this almost rectilinear frequency response in the operating range for a similar frequency response, especially the damping can be largely balanced, in the irradiated examination area. By this circuit and the converter used, a change of the frequency used for examination is possible without a change in sound heads. Further, in the evaluation of spectra for material characterization, especially in the tissue characterization, the respectively optimum ratio of space resolution and frequency resolution can be selected.

The process according to the invention can advantageously be performed by a circuit, which exhibits a multielement converter with phase-delayed, actuated converter elements, to perform a phase-array or a dynamically focused process. In this circuit, the output of a function generator is connected by an n-path signal divider, n computer-controlled delay circuits and n T/R switches, controlled by the function generator or a computer, to the inputs of n acoustically highly damped, electrically matched, broadband converter elements, whose outputs are connected by n T/R switches each to an m-path signal divider. These m-path signal dividers are each connected by m delay circuits and m fixed or variable circuits for frequency band selection and further by a circuit for in-phase summation and optionally signal distribution to a system for selective further processing of m frequency bands.

In another achievement of the object of the invention, a material is introduced in the examination area to be acoustically irradiated with which nonlinear oscillations are produced in this area by irradiated ultrasonic waves, a broadband, acoustically highly damped, electrically matched ultrasonic converter with one or more controllable converter elements individually or assembled in groups is excited by two HF bursts, whose respective excitation frequencies are different from one another, and are smaller than half the frequency upper limit of the operating range, and signal combinations of both excitation frequencies, especially their sum or difference frequency, are evaluated from the ultrasonic signals received from the ultrasonic converter, reflected from the examination area or backscattered from the latter.

In this case, a stronger receiving signal with a frequency of the combination of the frequencies of the irradiated signals, especially the sum or difference frequency, is obtained by irradiation of two signals separated from one another. In this case, the sum frequency is especially of interest because of the achievably higher space resolution. In this process, a converter element can be excited by two HF bursts. But the possibility also exists of exciting two separate converter elements respectively with one HF burst, and the center frequencies of these HF bursts vary and are smaller than half the upper limit of the frequency of the operating range.

By the nonlinearity produced according to the invention, a stronger receiving signal at $f_o + f_p$, i.e., at about 4 MHz, is obtained, for example, with two low-frequency signals, e.g., $f_o \approx f_p \approx 2$ MHz, than if only one sending signal of frequencies $f_o + f_p$ is used with same total output $I_o$, $I_p$. This phenomenon makes possible a higher penetration depth at high observation frequencies.

As materials or media, which produce the nonlinearity, the same can be used as in the process for evaluating the harmonic frequencies of the excitation frequency. Basically, the same circuit elements can be used with addition of a second HF generator.

In the circuit with a multielement converter, the second signal is always sent only in the respective direction of the first signal to reduce the average output irradiated in the examination area and is begun about 1 to 2 periods earlier and lasts until the end of the first burst signal. To achieve this, the second signal from the second generator is influenced by corresponding delay circuits so that it reaches the same converter elements in the sound head after passage of the T/R switch and is radiated in the same direction as the first sending signal. The circuit matrix then receives signals in the frequency sum. In this case, the T/R switch is controlled by the longer-lasting second sending signal.

Embodiments of the invention are to be explained in the following description with reference to the figures of the drawings.

There are shown in.

Figure 1:
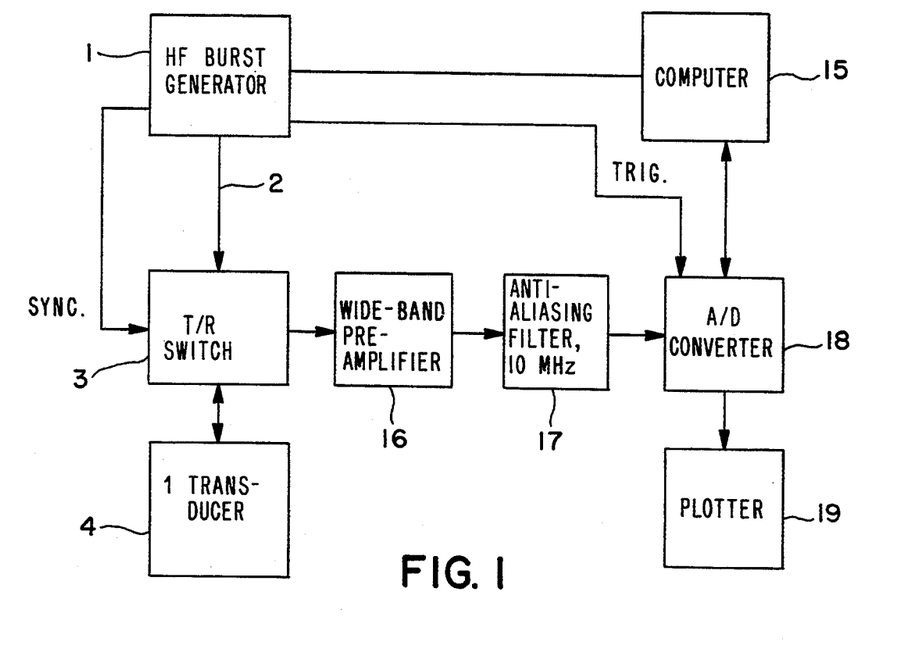
FIG. 1, a block diagram.
Figure 2:
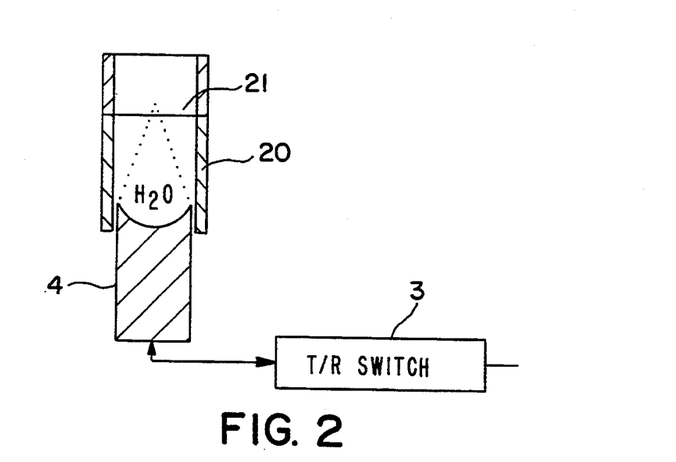
FIG. 2, a diagrammatic sectional representation of a test vessel.
Figure 3:
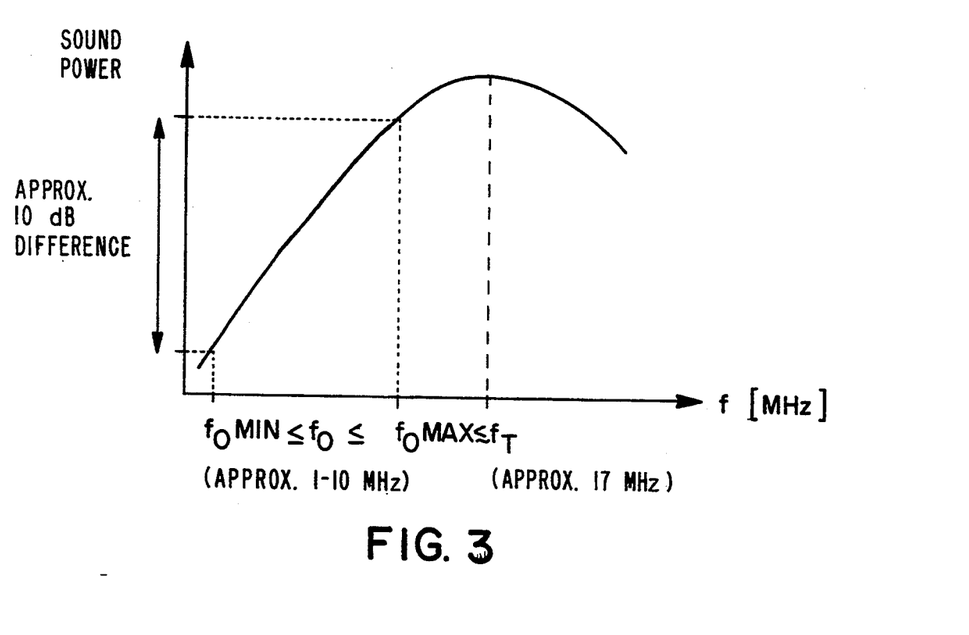
FIG. 3, a representation of the acoustic power curve of the converter as a function of the frequency, FIGS. 4-9, graphic representations of the backscatter spectrum and FIG. 10, another block diagram.

For the production of the signals provided for further processing, represented in FIGS. 4-9, the circuit represented in FIG. 1 is used together with the test vessel represented in FIG. 2, and the broadband sound head exhibits the power characteristic represented in FIG. 3.

Periodically repeated, electric sending pulses—HF bursts—of variable frequency $f_o$ in operating range $f_o$ min ... $f_{omax}$, ($f_o$, min=0.3 MHz<$f_o$<$f_{omax}$=22 MHz) and variable bandwidth, given by number n of sine periods per burst: 0.5<n<20 with adjustable amplitude, are produced by a function generator 1, which is controlled by central computer 15. This central computer 15 controls both the course of the measurement and its evaluation. Output 2 of generator 1 leads to a sending-receiving switch 3, which, as diagrammatically represented, is synchronized by generator 1. T/R switch 3 can also be controlled directly by computer 15. Output 2 of T/R switch 3 is connected to a broadband, matched and focused converter element 4. The special features of this converter element 4 are diagrammatically represented in FIG. 3. This converter exhibits a large wideband without disturbing resonances in the operating range, further, a good electrical and acoustic impedance matching and a transmitter center frequency $f_r > f_{o\ max}$. In the described example, $f_t = 17$ MHz. This converter can also exhibit spatially and electrically separated sending and receiving converter elements. In this case, T/R switch 3 is unnecessary. In addition, another converter element for sending a second, independent high-frequency signal can be advantageously provided.

The signal received from converter element 4 is fed by the reversed T/R switch to a broadband input amplifier 16, which, in digital frequency analysis, is downstream from an antialiasing filter 17. Broadband input amplifier 16 exhibits a bandwidth $> f_{o\ max}$. Filter 17 has, for example, a cutoff frequency of 10 MHz. A rapid A/D converter, in which the signal is digitalized, for example with a Nyquist frequency of 12.5 MHz, is downstream from filter 17. The further processing of the signals takes place in a digital storage oscilloscope and in the central computer. Plotter 19 is downstream from A/D converter 18.

FIG. 1 shows that the A/D converter is triggered by function generator 1.

The digitalized signal is stored and further processed in a way known in the art. It is available especially for necessary corrections. Before the A/D conversion, a signal, which is digitalized only after analog further processing, can also be branched off.

FIG. 2 diagrammatically shows the geometry of test vessel 20, with which the measuring results represented below are achieved.

As FIG. 2 shows, sound head 4 is placed in test vessel 20. It is a 17 MHz sound head, which is broadband, matched and focused. Water is in test vessel 20. Two sheets 21 separate a test area, in which 10 mg of ultrasonic contrast medium is dissolved in 3 ml of $H_2O$.

The signals reflected and/or backscattered in the measuring area between sheets 21 contain special portions which were obtained by an interaction between the sending pulse (at $f_o$) and the nonlinear contrast medium introduced in the measuring object.

FIG. 3 diagrammatically shows the frequency band of the converter element in the sound head. It can be seen that in the operating range, the frequency response of the oscillator in the sound head is almost linear. The frequency response in the operating range can be used to balance a similar frequency response in the test piece. But the frequency response in the test piece can also be corrected later by a weighting.

Figure 4:
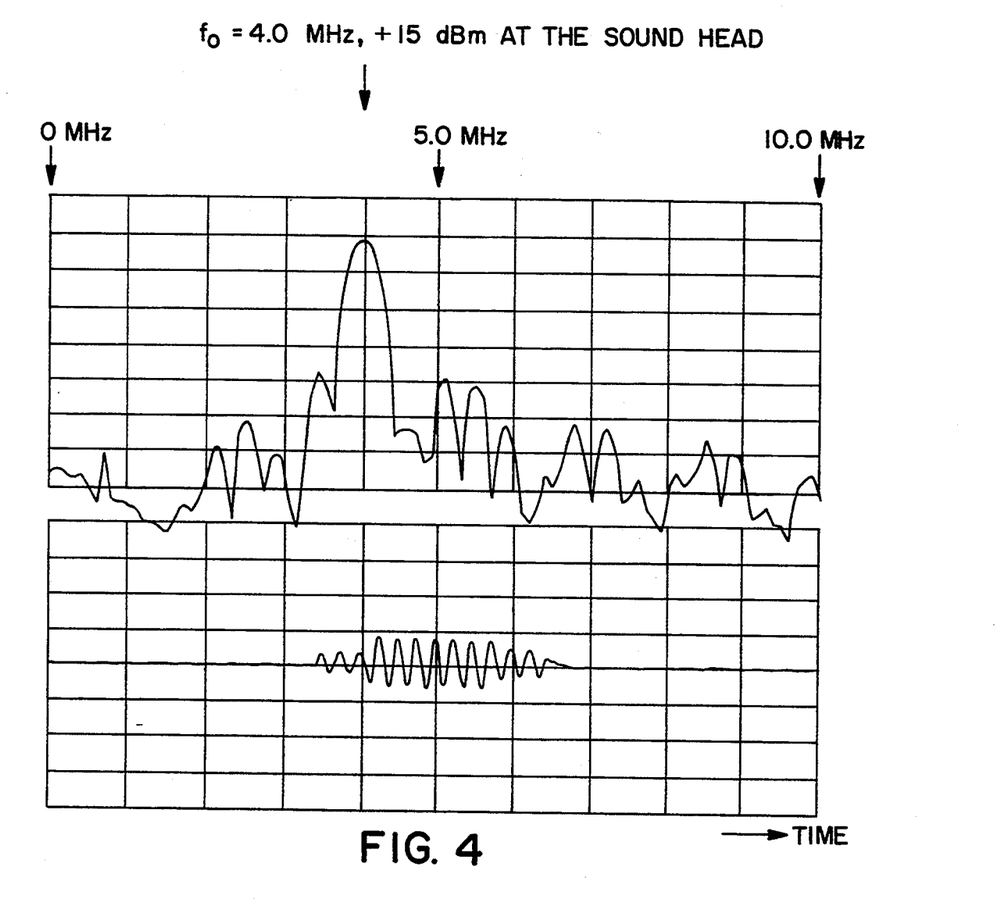

In measuring, an advantageous period is selected in the time range by a computer-controlled gate circuit, not shown. Several periods can also be selected. The related spectrum is calculated by an FFT circuit (Fast Fourier Transformation) and examples of such spectra are represented in FIGS. 4–9. By the selection of a corresponding time window length, a choice can be made between optimum frequency resolution and optimum high-sensitivity resolution. In FIGS. 4–8, the spectrum in each case is represented by the time window. To bring out clearly the spectral components in these figures, a long time window, i.e., a poor high-sensitivity resolution, was selected. FIG. 4 illustrates the time characteristic of the sending pulse after a reflection on the exciting window without contrast medium, $f_o = 4.0$ MHz, $+15$ dBm on the sound head. A clear signal can be detected at 4 MHz. The signal represented in the upper part of FIG. 4 is an averaged output spectrum, which was obtained behind the low-pass filter with a Nyquist frequency of 50 MHz.

Figure 5:
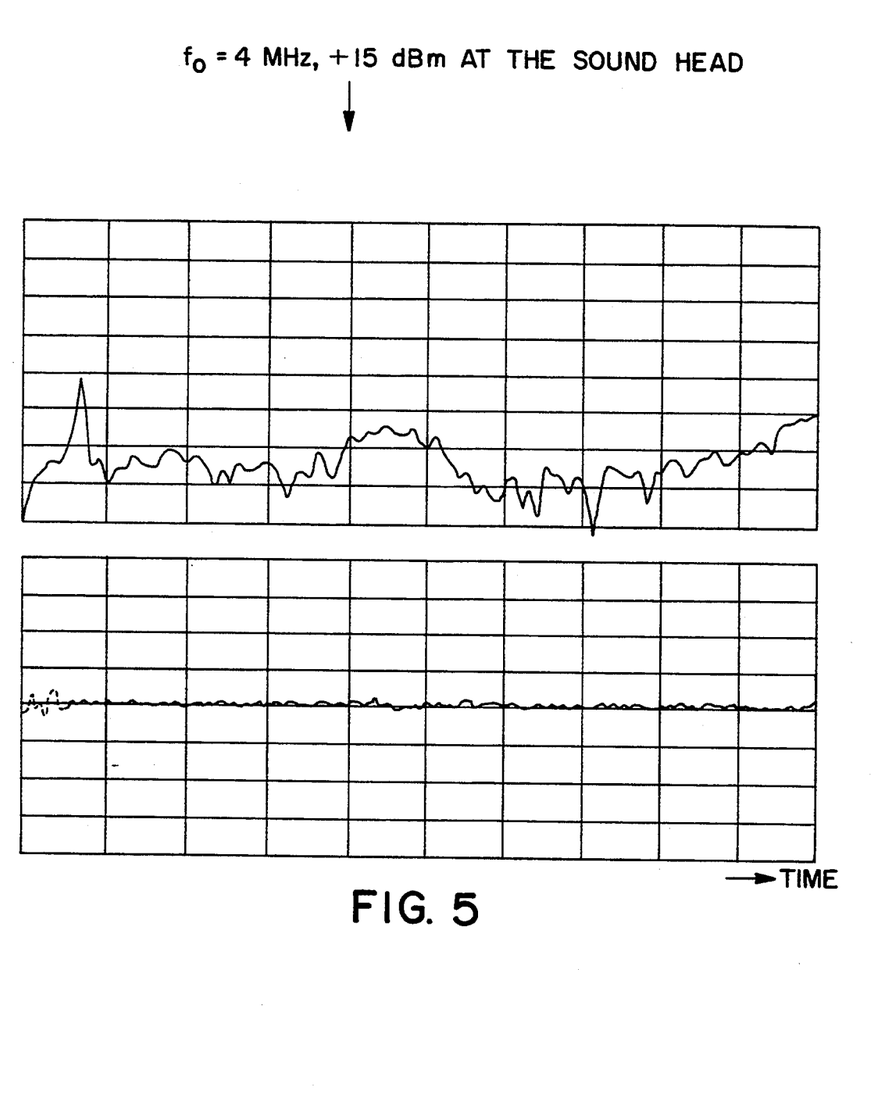
Figure 6:
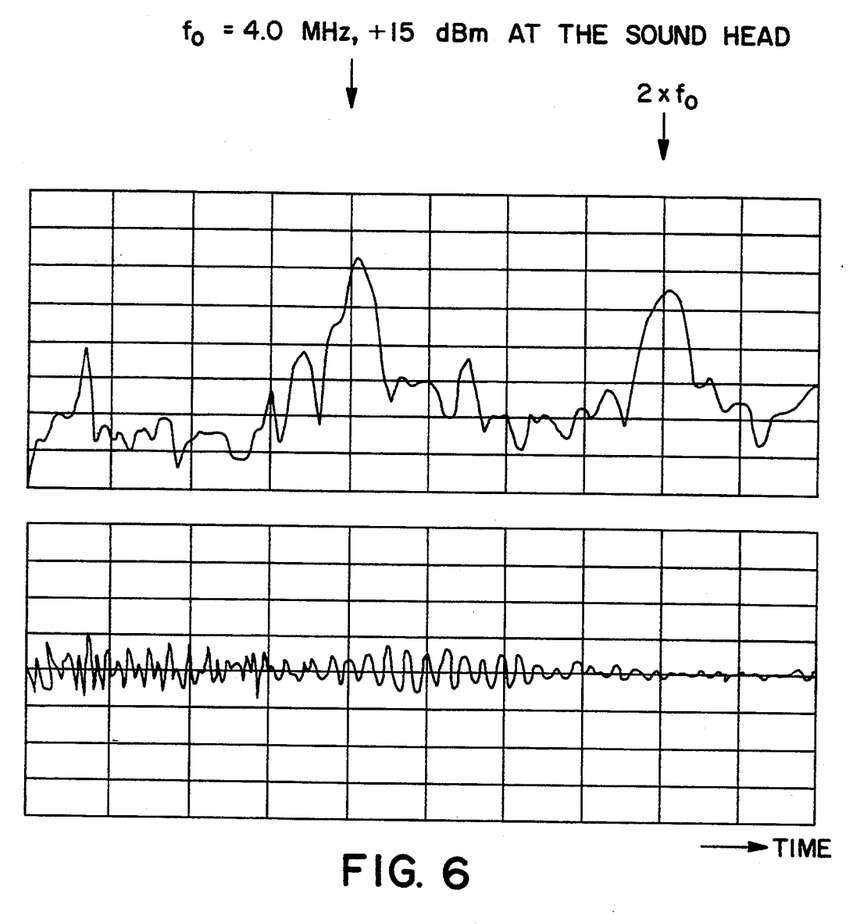

In FIG. 5, the backscatter signal from the test chamber is represented without an ultrasonic contrast medium. FIG. 6 shows the backscatter signal seven minutes after adding 10 mg of contrast medium in 3 ml of $H_2O$. A clear peak can be detected at $2 \times f_o$.

Figure 7:
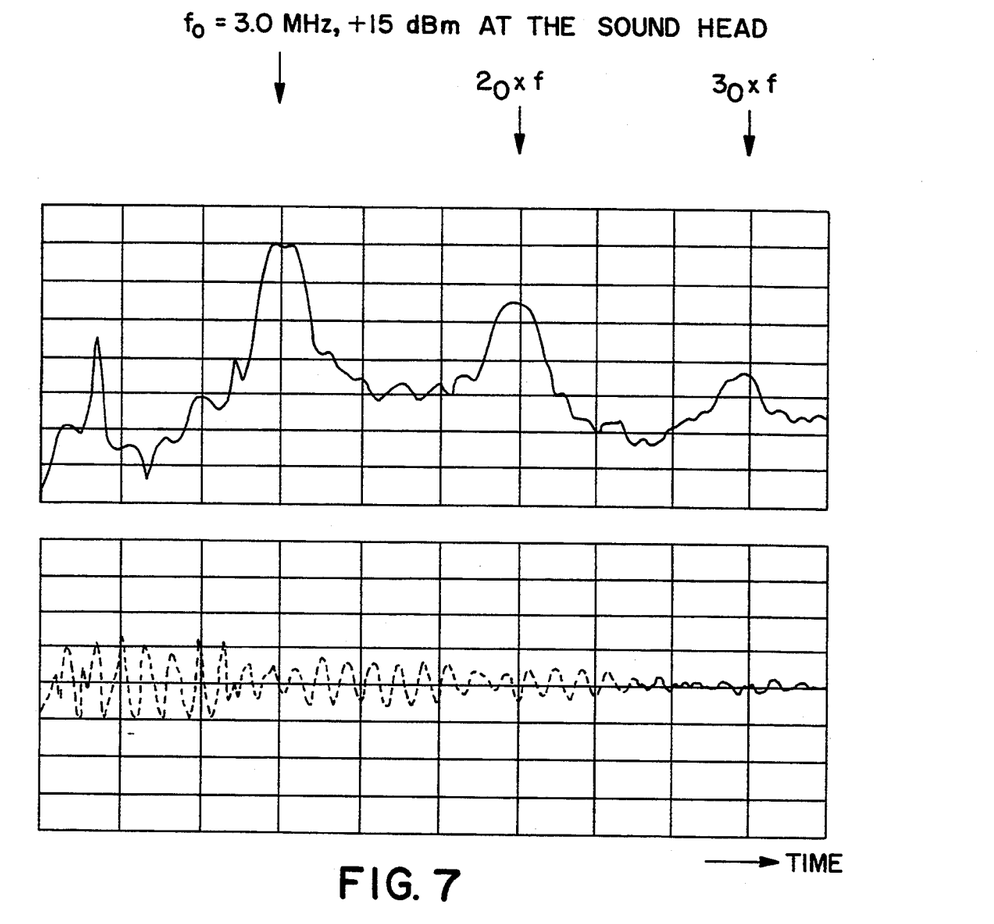
Figure 8:
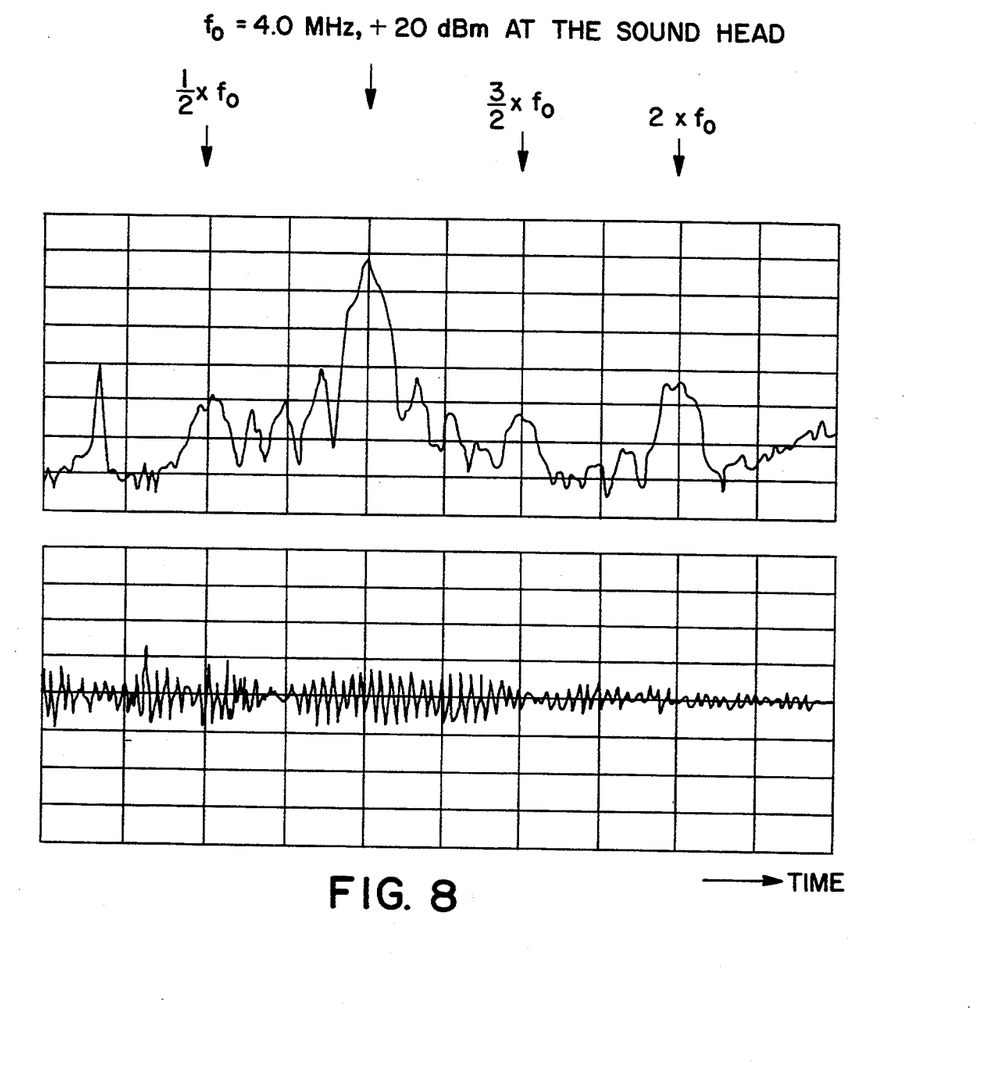

FIG. 7 shows a measurement after 21 minutes under the conditions represented in FIG. 5. The operation was performed with a frequency $f_o = 3$ MHz. The received spectrum clearly shows the first and second harmonics at 6.0 and 9.0 MHz. FIG. 6 illustrates the backscatter signal 15 minutes after adding an ultrasonic contrast medium of smaller concentration. The operation was performed on the sound head with a frequency, $f_o$, of 4 MHz $+20$ dBm. The spectrum represented in the upper part of FIG. 8 shows, with higher frequency resolution, subharmonics at $\frac{1}{2} f_o$, ultraharmonics at $3/2 f_o$ and the first harmonics at $2 f_o$.

Figure 9:
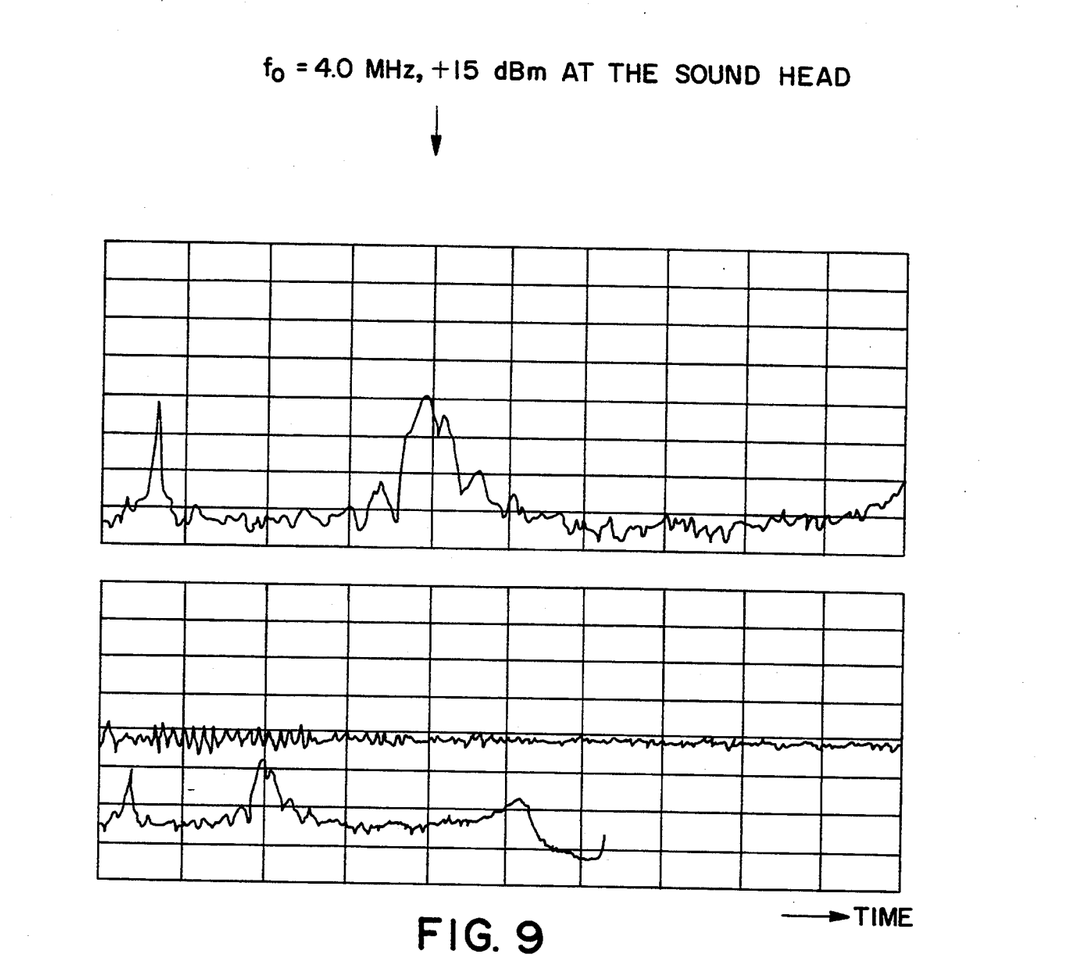

FIG. 9 shows a backscatter signal of linear ultrasonic contrast medium $f_o = 4$ MHz $+15$ dBm on the sound head. The spectrum shows only a backscattering in the excitation frequency.

Figure 10:
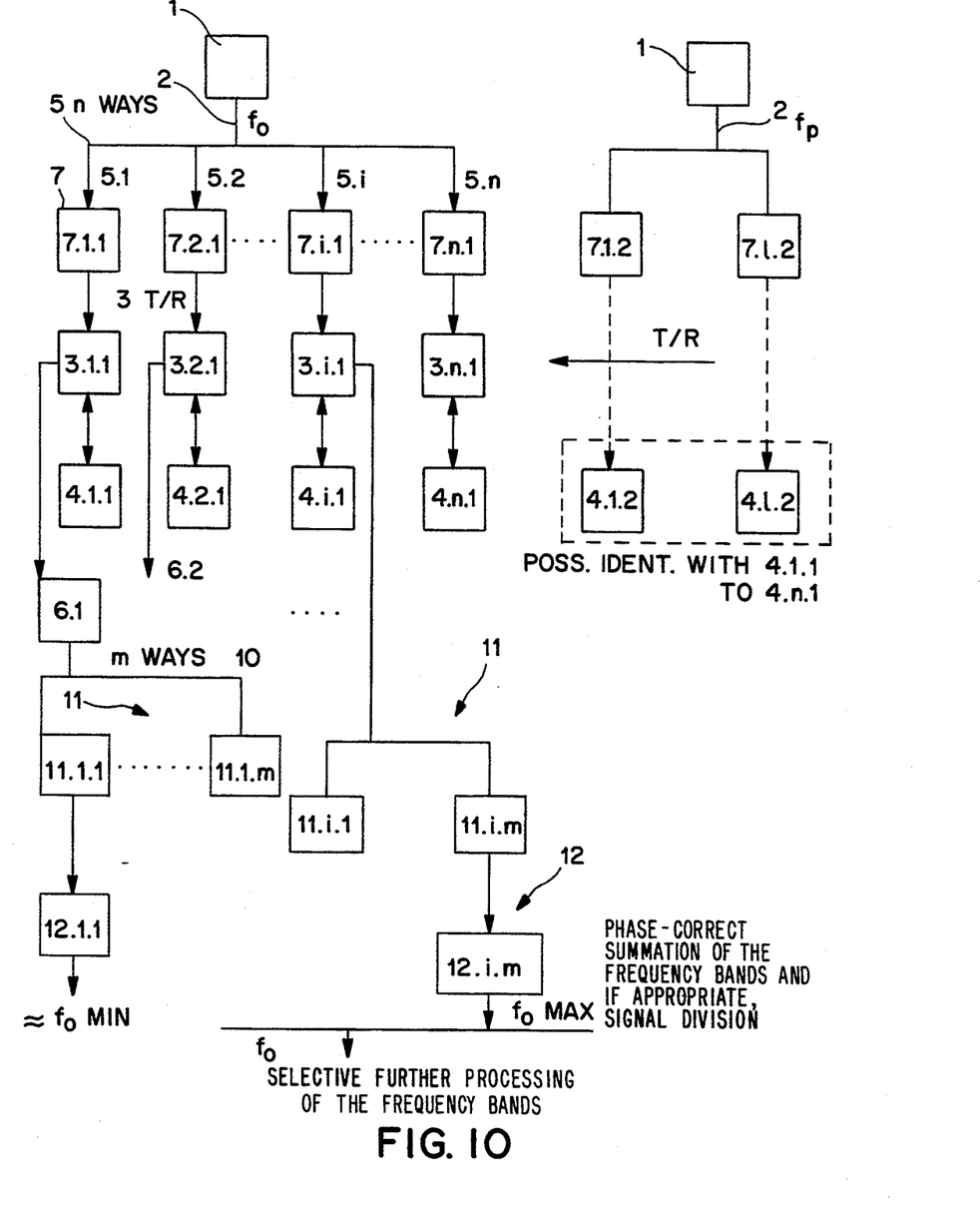

It can be seen that the represented spectra exhibit clear amplitudes in the frequency ranges which do not occur in the sending spectrum if an interaction has taken place with a nonlinear contrast medium. Spectral changes can be evaluated, which are caused by a Doppler effect. To use the circuit used in the described embodiments for the imaging ultrasonic processes, additional components are provided, if a sound head of "phased array" type or a dynamically focused sound head is used. Such a block diagram is illustrated in FIG. 10.

The sending signal of function generator 1 (frequency $f_o$) is fed from output 2 to n path signal divider 5. The distribution takes place with one branch each per converter element. In the represented embodiment, n converter elements 4 are provided. Actuation of these converter elements 4.1 ... 4.n takes place by delay circuits 7.1 ... 7.n and T/R switches 3.1 ... 3.n controlled by the generator or computer. The delay periods are set for each converter element by the computer so that the desired directional characteristic on the sound head results in the selected sending frequency. The same directional characteristic is set by the computer by corresponding delays in the receiving part. The signal received from sound heads 4.1 ... 4.n is fed by T/R switches 6.1, ..., 6.n actuates an m-path signal divider 10, to which correspondingly controlled or set delay circuits 11 are placed downstream in each case, which supplies circuits 12 for frequency band selection. Circuits for in-phase summation of the frequency bands and for optional signal distribution are downstream. A selective further processing of the individual frequency bands with the process known in the art follows.

Especially, an evaluation of the frequencies, which are not identical with $f_o$, for example, $\frac{1}{2} f_o$, $2 f_o$, takes place.

The delay circuits can be variable or fixed. The distribution of the received signals to the m-path signal dividers produces the desired number of frequency bands, whose position and width are set with band filters. As an alternative, the distribution can also take place so that the receiving signal, with a subsidiary signal that is different depending on the frequency band and derived from a sending signal, is mixed so that the individual bands in the following stages can operate with homogeneous components.

The frequency band around $f_o$ yields the usual results, while the other bands contain strongly frequency-shifted and nonlinear signal portions from interactions of the sending signal with the nonlinear ultrasonic contrast media.

The further processing steps and signal analyses could take place in any frequency channel or in several parallel frequency channels according to the known processes.

To use two sending frequencies $f_o$ and $f_p$, the second generator, represented on the right side of FIG. 10, is provided, which is connected by signal dividers and delay lines 15 to T/R switches 3.1 ... 3.n. Second generator 1 makes it possible acoustically to irradiate at least the space area in the test object, which is determined by the instantaneous directional characteristic and the receiving gate. The design can be such that in addition to the described broadband converter elements, at least one also broadband sending converter is located in the sound head, which is preferably separated electrically from the others and which is fed by second, independent sending generator 1. But both sending signals can also be superposed electrically so that the same converter elements can be used.

We claim:

1. An ultrasonic process for imaging and, optionally, for evaluation of a Doppler spectrum, of an object having limited resistance to sonic energy, in an inspection zone, which comprises:

introducing into the inspection zone, the object to be imaged and an ultrasonic contrast medium that contains microbubbles as scattering bodies or that produces microbubbles upon exposure to ultrasonic waves, such that the contrast agent provides nonlinear vibrations of the microbubbles when irradiated in the inspection zone by irradiated ultrasonic waves, applying an HF burst of excitation frequency, $f_o$, to electrically excite a wide-band, acoustically highly damped, electrically matched ultrasonic transducer having a transducer element or having several transducer elements, controllable individually or in groups, and thereby exposing the inspection zone to ultrasonic waves, $f_o$, of 1 MHz to 22 MHz, and receiving by the ultrasonic transducer, the ultrasonic signal reflected from the inspection zone and scattered back from that zone, and processing the received ultrasonic signal for further evaluation, evaluating from the reflected and backscattered ultrasonic signal at least one of the harmonics, the subharmonics and the ultraharmonics of the excitation frequency, $f_o$, and, optionally, the excitation frequency $f_o$.

2. An ultrasonic process for imaging and, optionally, for evaluation of a Doppler spectrum, of an object having limited resistance to sound energy, in an inspection zone, which comprises:

introducing into the inspection zone the object to be imaged and an ultrasonic contrast agent that contains microbubbles as scattering bodies or that produces microbubbles upon exposure to ultrasonic waves, such that the contrast agent provides nonlinear vibrations of the microbubbles when irradiated in the inspection zone by ultrasonic waves, applying two HF bursts of excitation frequencies, $f_o$ and $f_p$, to electrically excite a wide-band, acoustically highly damped, electrically matched ultrasonic transducer having a transducer element or having several transducer elements, controllable individually or in groups, wherein the excitation frequencies, $f_o$ and $f_p$, are different and are each less than half the upper frequency limit of the working range of the ultrasonic transducer, and receiving by the ultrasonic transducer the ultrasonic signal reflected from the inspection zone and scattered back from that zone, and processing the received ultrasonic signal for further evaluation, evaluating from the reflected and backscattered ultrasonic signal the sum or the difference of the two excitation frequencies.

3. The ultrasonic process according to claim 1, wherein the ultrasonic contrast agent is a solution, an emulsion or a suspension.

4. The ultrasonic process according to claim 3, wherein the contrast agent is a microbubble suspension having a concentration of from $10^{-3}\%$ by weight to 30% by weight dry substance in the suspension medium.

5. The ultrasonic process of claim 1, wherein the ultrasonic transducer is electrically excited by at least one function generator by means of which HF bursts of adjustable amplitude and adjustable excitation frequency, $f_o$, 1 MHz to 22 MHz, with 0.5 to 30 cycles are generated.

6. The ultrasonic process of claim 5, wherein the excitation frequency, $f_o$, is 1 MHz to 11 MHz and 1 to 5 cycles are generated.

7. The ultrasonic process of claim 2, wherein the two HF bursts are generated by two function generators and fed either to one ultrasonic transducer element or to two ultrasonic transducer elements, and wherein each function generator generates HF bursts of adjustable amplitude and adjustable excitation frequency, $f_o$ or $f_p$, of 0.5 to 20 MHz with from 1 to 25 cycles.

8. The ultrasonic process of claim 7, wherein the excitation frequency, $f_o$ or $f_p$, is 1 to 5 MHz and 1 to 10 cycles are generated.

9. The ultrasonic process of claim 1, wherein, from the reflected and backscattered ultrasonic signal, frequencies that are lower than the after frequency ($f_r$) of the ultrasonic transducer are evaluated.

10. The ultrasonic process of claim 1, wherein the evaluation is carried out by means of a computer-controlled gate circuit, at least one time window being selected and the associated frequency spectrum being determined in analog or digital manner.

11. The ultrasonic process of claim 10, wherein the length of the time window and the number of cycles per burst are adjusted according to a selected frequency resolution and spatial resolution.

12. The ultrasonic process according to claim 2, wherein the ultrasonic contrast agent is a solution, an emulsion or a suspension.

13. The ultrasonic process according to claim 12, wherein the contrast agent is a microbubble suspension having a concentration of from $10^{-3}\%$ by weight to 30% by weight dry substance in the suspension medium.

14. The ultrasonic process of claim 2, wherein the evaluation is carried out by means of a computer-controlled gate circuit, at least one time window being selected and the associated frequency spectrum being determined in analog or digital manner.

15. The ultrasonic process of claim 14, wherein the length of the time window and the number of cycles per burst are adjusted according to a selected frequency resolution and spatial resolution.

16. A circuit for carrying out the ultrasonic process of claim 1 comprising:

an ultrasonic transducer having n ultrasonic transducer elements which receive signals in phase-delayed manner, a function generator, the output (2) of which is connected by way of an n-way signal divider (5), to n computer-controlled time-delay circuits (7.1.1 . . . 7.n.1)

and n transmitter/receiver switches (3.1.1 . . . 3.n.1) controlled by the function generator (1) or by a computer, connected to the inputs of the ultrasonic transducer elements, the outputs of the ultrasonic transducer elements connected, by way of the n transmitter/receiver switches (3.1.1 . . . 3.1.n), each to a further m-way signal divider (10) which divides the signals m number of ways, the m-way signal dividers (10) being connected by way of m time-delay circuits (11), by way of m fixed or variable circuits (12) for frequency band selection and by way of a circuit for phase-correct summation and signal division to a system for the selective further processing individually or in parallel—of m frequency bands.

17. A circuit for carrying out the ultrasonic process of claim 2 comprising:

an ultrasonic transducer having n ultrasonic transducer elements which receive signals in phase-delayed manner, first and second function generators, the outputs of which are connected by way of two n-way signal dividers, to n computer-controlled time-delay circuits (7.1.1 . . . 7.n.1)

and n transmitter/receiver switches (3.1.1 . . . 3.n.1) controlled by the function generator (1) or by a computer, connected to the inputs of the ultrasonic transducer elements, the outputs of the ultrasonic transducer elements connected, by way of the n transmitter/receiver switches (3.1.1 . . . 3.1.n), each to a further m-way signal divider (10) which divides the signals m number of ways, the m-way signal dividers (10) being connected by way of m time-delay circuits (11), by way of m fixed or variable circuits (12) for frequency band selection and by way of a circuit for phase-correct summation and signal division to a system for the selective further processing—individually or in parallel—of m frequency bands.

* * * * *

(12) EX PARTE REEXAMINATION CERTIFICATE (6458th)
United States Patent
Uhlendorf et al.

(10) Number: US 5,410,516 C1
(45) Certificate Issued: Oct. 7, 2008

(54) ULTRASONIC PROCESSES AND CIRCUITS FOR PERFORMING THEM

(75) Inventors: Volkmar Uhlendorf, Berlin (DE); Thomas Fritzsch, Berlin (DE); Joachim Siegert, Berlin (DE)

(73) Assignee: Schering Aktiengesellschaft, Berlin und Bergkamen (DE)

Reexamination Request:
No. 90/008,612, Apr. 27, 2007

Reexamination Certificate for:
Patent No.: 5,410,516
Issued: Apr. 25, 1995
Appl. No.: 08/076,221
Filed: Jun. 14, 1993

Related U.S. Application Data

(63) Continuation of application No. 07/684,900, filed on Mar. 9, 1992, now abandoned.

(30) Foreign Application Priority Data

Sep. 1, 1988 (DE) ............................................. 3829999

(51) Int. Cl.
*G03B 42/06* (2006.01)

(52) U.S. Cl. ......................................................... 367/7
(58) Field of Classification Search ........................ None
See application file for complete search history.

(56) References Cited

U.S. PATENT DOCUMENTS

| | | | | |
|---|---|---|---|---|
| 4,442,843 A | * | 4/1984 | Rasor et al. | 424/9.52 |
| 4,702,258 A | | 10/1987 | Nicolas et al. | |
| 4,714,846 A | | 12/1987 | Pesque et al. | |

OTHER PUBLICATIONS

Volkmar Miszalok, Thomas Fritzsch and Michael Schartl "Myocardial Perfusion Defects In Contrast Echocardiograph: Spatial And Temporal Localisation" *Ultrasound in Med. & Biol.* vol. 12, No. 7, pp. 581–586 1986.
V. G. Welsby and M. H. Safar "Acoustic Non–Linearity Due to Micro–Bubbles in Water*" *Based on paper presented at Meeting on "Various Physical Aspects of Cavtiation" at Imperial College, London,* Jun. 14, 1968. *Acustica* vol. 22 (1969/70); pp. 177–182.
Karrer et al, (Hewlett–Packard Journal, Oct. 1983, pp. 3–6).
Miller, Hewlett–Packard Journal, Oct. 1983, pp. 22–26.
Snyder et al., Hewlett–Packard Journal, Oct. 1983, pp. 34–40.
Gatzke et al., Hewlett–Packard Journal, Dec. 1983, pp. 13–20.
Larson, Hewlett–Packard Journal, Oct. 1983, pp. 17–22.
Leavitt et al, Hewlett–Packard Journal, Oct. 1983, pp. 30–34.
Szabo et al, Hewlett–Packard Journal, Oct. 1983, pp. 26–29.
Banks, Hewlett–Packard Journal, Oct. 1983, pp. 6–11.
Becher and Burns, Handbook of Contrast Echocardiography, Springer, Berlin, 2000, p. 36–38.

* cited by examiner

*Primary Examiner*—Beverly M. Flanagan (57) ABSTRACT

A process for selective graphic representation and/or evaluation of the Doppler spectrum of objects limitedly resistant to sonic intensity, for example biological organs and tissues, by an ultrasonic process wherein a material is introduced in the examination area to be acoustically irradiated, nonlinear oscillations are produced in the examination area by irradiated ultrasonic waves and the signal is evaluated by an ultrasonic converter. Also, a circuit for carrying out the above process is disclosed.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 6, lines 14–25:

FIG. 7 shows a measurement after 21 minutes under the conditions represented in FIG. 5. The operation was performed with a frequency $f_0$=3 MHz. The received spectrum clearly shows the first and second harmonics at 6.0 and 9.0 MHz. FIG. [6] *8* illustrates the backscatter signal 15 minutes after adding an ultrasonic contrast medium of smaller concentration. The operation was performed on the sound head with a frequency $f_0$ of 4 MHz+20 dBm. The spectrum represented in the upper part of FIG. 8 shows, with higher frequency resolution, subharmonics at ½ $f_0$, ultraharmonics at 3/2 $f_o$ and the first harmonics at 2 $f_0$.

AS A RESULT OF REEXAMINATION, IT HAS BEEN DETERMINED THAT:

The patentability of claims 1, 3–6, 10 and 11 is confirmed.

New claims 18–20 are added and determined to be patentable.

Claims 2, 7, 8, 9 and 12–17 were not reexamined.

*18. The ultrasonic process of claim 1 for imaging a patient to whom a contrast agent has been administered.*

*19. The ultrasonic process of claim 18 wherein the intensity of the ultrasonic waves is effective to image said patient using said signals generated by nonlinearity of the contrast agent but is ineffective to generate nonlinear signals sufficient to image said patient in the absence of a contrast agent.*

*20. The ultrasonic process of claim 18 wherein the intensity of the ultrasound energy is effective to create in water substantial signals generated by nonlinearity of the contrast agent but is ineffective to generate in water substantial nonlinear signals in the absence of a contrast agent.*

\* \* \* \* \*